United States Patent [19]
Cohen

[11] Patent Number: 5,879,620
[45] Date of Patent: Mar. 9, 1999

[54] STERILIZATION WRAP AND PROCEDURES

[75] Inventor: Bernard Cohen, Duluth, Ga.

[73] Assignee: Kimberly-Clark Worldwide, Inc., Neenah, Wis.

[21] Appl. No.: 969,590

[22] Filed: Nov. 13, 1997

[51] Int. Cl.$^6$ .................... A61L 2/00; A61L 9/00
[52] U.S. Cl. .................. 422/1; 206/439; 422/40; 422/294; 422/300; 428/361
[58] Field of Search ............. 428/36.1; 422/300, 422/302, 297, 1, 40, 294; 206/438–441

[56] References Cited

U.S. PATENT DOCUMENTS

| | | | |
|---|---|---|---|
| 4,041,203 | 8/1977 | Brock et al. | 428/157 |
| 4,346,710 | 8/1982 | Thanawalla et al. | |
| 4,714,595 | 12/1987 | Anthony et al. | |
| 4,801,427 | 1/1989 | Jacob. | |
| 4,813,210 | 3/1989 | Masuda et al. | |
| 5,151,321 | 9/1992 | Reeves et al. | |
| 5,290,613 | 3/1994 | Shuetz et al. | |
| 5,401,446 | 3/1995 | Tsai et al. | |
| 5,459,978 | 10/1995 | Weiss et al. | 206/439 |
| 5,498,463 | 3/1996 | McDowell et al. | |
| 5,549,868 | 8/1996 | Carlson, II. | |
| 5,616,408 | 4/1997 | Oleszczuk et al. | |
| 5,620,785 | 4/1997 | Watt et al. | 428/219 |
| 5,645,057 | 7/1997 | Watt et al. | |

FOREIGN PATENT DOCUMENTS

WO 94/00166  1/1994  WIPO.

OTHER PUBLICATIONS

Jacobs, Paul T., Ph.D., "Plasma Sterilization," ETO Alternative 1995.

"ZELEC KC antistat," Bulletin from Dupont Chemicals Material Safety Data Sheet, Oct. 8, 1987.

*Primary Examiner*—Krisanne Thornton
*Attorney, Agent, or Firm*—Jones & Askew LLP; Nancy M. Klembus

[57] ABSTRACT

A sterilization device which includes an inner sterilization wrap and a re-usable outer sterilization bag. The re-usable outer sterilization bag has an outside surface and an inside surface defining a pouch with an opening for receiving the inner sterilization wrap and a sterilizable object. The material is preferably a spunbonded or meltblown polyolefin fiber non-woven breathable web. Also provided are methods of sterilizing an object, and methods of using a sterilizable bag.

38 Claims, No Drawings

STERILIZATION WRAP AND PROCEDURES

FIELD OF THE INVENTION

This invention relates in general to the field of materials suitable for sterilizing and containing objects, typically for use in the medical industry.

BACKGROUND OF THE INVENTION

The sterilization of medical equipment and supplies is vital to minimizing the spread of harmful or infectious agents to patients. The medical equipment or supplies in need of sterilization include, for example, clamps, scalpel blade handles, retractors, forceps, scissors, basins or towels. Typically, the object desired to be sterilized is placed on an instrument tray and packaged within at least one layer of a sterilization wrap. The wrapped object is then sterilized within the sterilization wrap by a variety of methods, e.g. steam autoclaving, plasma sterilization, microwave irradiation, etc. Sterility of the object is typically maintained by keeping the sterilization wrap package sealed until immediately prior to use.

In the field of sterilization wraps, many designs have been provided which attempt to permit the penetration of a sterilant therethrough, while minimizing the subsequent entry of any contaminates. The type of sterilization technique employed may dictate the materials used. For, example, where gamma or other radiation is used to sterilize the contents, the sterilization wrap may be sealed and made impermeable to even gases. However, when plasma sterilization, steam, ethylene oxide or other attenuating gases, are used to sterilize an item, the sterilization wrap must be gas permeable or breathable. This presents a challenge to construct a breathable sterilization wrap that minimizes the entry of any contaminates, e.g. bacteria, following the sterilization procedure.

Many prior art sterilization wraps require permanent sealing of the sterilization wrap around the object to be sterilized. Therefore, in order to access and use the sterilized object, these prior art sterilization wraps must be torn open. Moreover, prior art sterilization wraps are typically sheets which are wrapped into position and secured by tape or other adhesive fastening means. An alternative approach would be to provide an outer sterilization wrap that maintains the wrapped conformation of the inner wrap. These and other objects of the invention will be apparent to those skilled in the art.

SUMMARY OF THE INVENTION

The present invention provides a sterilization device comprising an inner sterilization wrap and a re-usable outer sterilization bag. The re-usable outer sterilization bag has an outside surface and an inside surface defining a pouch with an opening for receiving the inner sterilization wrap and a sterilizable object. The material is preferably a spunbonded or meltblown polyolefin fiber non-woven, breathable web. The present invention also provides methods of sterilizing an object, and methods of using a sterilizable bag.

DETAILED DESCRIPTION OF THE INVENTION

As used herein the term "sterilization" refers to a wide variety of techniques employed to attenuate, kill or eliminate infectious agents. For example, sterilization contemplates gas plasma sterilization, such as described in U.S. Pat. No. 4,801,427, in addition to steam sterilization, ethylene oxide sterilization, and irradiation.

As used herein the term "polymer" generally includes but is not limited to, homopolymers, copolymers (such as for example, block, graft random and alternating copolymers), terpolymers, etc. and blends and modifications thereof. Furthermore, unless otherwise specifically limited, the term "polymer" shall include all possible geometrical configurations of the material. These configurations include, but are not limited to isotactic, syndiotactic and random symmetries.

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes.

As used herein the term "spunbonded fibers" refers to small diameter fibers which are formed by extruding molten thermoplastic polymer material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. Nos. 3,502, 763 and 3,909,009 to Levy, and U.S. Pat. No. 3,542,615 to Dobo et al. Spunbonded fibers are generally continuous and larger than 7 microns, more particularly, having an average diameter of greater than 10 microns.

As used herein the term "meltblown fibers" means fibers formed by extruding a molten thermoplastic polymer through a plurality of fine, usually circular, die capillaries as molten threads or filaments into a high velocity gas (e.g. air) stream which attenuates the filaments of molten thermoplastic polymer material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 and U.S. Pat. No. 3,978,185.

The meltblowing process generally uses an extruder to supply melted polymer to a die tip where the polymer is fiberized as it passes through fine openings, forming a curtain of filaments. The filaments are drawn pneumatically and deposited on a moving foraminous mat, belt or "forming wire" to form the nonwoven fabric. Nonwoven fabrics may be measured in ounces per square yard (osy) or grams per square meter (gsm). (Multiplying osy by 33.91 yields gsm.)

The fibers produced in the meltblowing process are generally in the range of from about 0.5 to about 10 microns in diameter, depending on process conditions and the desired end use for the fabrics to be produced from such fibers. For example, increasing the polymer molecular weight or decreasing the processing temperature results in larger diameter fibers. Changes in the quench fluid temperature and pneumatic draw pressure can also affect fiber diameter. Finer fibers are generally more desirable as they usually produce greater barrier properties in the fabric into which they are made.

The fabric of this invention may be used in a single layer embodiment or as a multilayer laminate incorporating the fabric of this invention. Such a laminate may be formed by a number of different techniques including but not limited to using adhesive, needle punching, ultrasonic bonding, print bonding, thermal calendering and any other method known in the art. Such a multilayer laminate may be an embodiment wherein some of the layers are spunbonded and some meltblown such as a spunbonded/meltblown (SM) laminate or a spunbonded/meltblown/spunbonded (SMS) laminate, as disclosed in U.S. Pat. No. 4,041,203 to Brock et al. and U.S. Pat. No. 5,169,706 to Collier, et al. or wherein some of the layers are made from staple fibers. The fibers used in the other layers may be polyethylene, polypropylene or bicomponent fibers. One useful source of such a SMS laminate is commercially available from the Kimberly-Clark Corporation as KIMGUARD® sterile wrap.

An SMS laminate, for example, may be made by sequentially depositing onto a moving conveyor belt or forming wire first a spunbonded fabric layer, then a meltblown fabric layer and last another spunbonded layer and then bonding the laminate in a manner described above. Alternatively, the three fabric layers may be made individually, collected in rolls, and combined in a separate bonding step.

In re-usable applications, when the fabric of this invention is an SMS laminate, it has been found to be advantageous to "prebond" one of the spunbonded layers. Pre-bonding is a step of (thermally) bonding a layer by itself using a pattern of 8 to 50% bond area or more particularly a pattern of about 25% bond area with many small pins. In these situations, pre-bonding is advantageous with polyolefin webs because of the relatively high heat of fusion and low melting point of polyolefin. It is believed that in order to supply enough heat to a polyolefin web to bond it, the heat addition must be done sufficiently slowly to avoid excessively melting the web and causing it to stick to the calendar rolls. Pre-bonding one of the spunbonded layers helps to reduce the intensity of temperature the laminate must be subjected to in the bonding step.

Pre-bonding also provides the material with greater abrasion resistance though it can reduce the drapeability somewhat. Since it is an objective of this invention that the material provide good barrier properties yet be soft and drapeable, pre-bonding should be kept to a minimum. Pre-bonding is optional, and if desired should be restricted to only one layer for this reason.

After pre-bonding, the spunbonded layer may then be combined with unbonded meltblown and spunbonded layers and bonded with a more open bond pattern like the one mentioned above, preferably with a pattern having relatively larger pins. The temperature of bonding will vary depending on the exact polymers involved, the degree and strength of bonding desired, and the final use of the fabric.

The layers of the fabric of this invention may also contain fire retardants for fire safety, or pigments to give each layer the same or distinct colors. Fire retardants and pigments for spunbonded and meltblown thermoplastic polymers are known in the art and are usually internal additives. A pigment, if used, is generally present in an amount less than 5 weight percent of the SMS composite.

The material of this invention may also have topical treatments applied to it for more specialized functions. Such topical treatments and their methods of application are known in the art and include, for example, alcohol repellency treatments, anti-static treatments and the like, applied by spraying, dipping, etc. An example of such a topical treatment is the application of ZELEC® antistatic neutralized mixed alkyl phosphates (available from E.I. DuPont, Wilmington, Del.).

The present invention provides a sterilization device comprising an inner sterilization wrap and a re-usable outer sterilization bag. The re-usable outer sterilization bag has an outside surface and an inside surface defining a pouch with an opening for receiving the inner sterilization wrap and a sterilizable object. In one embodiment, the bag may be formed from a single sheet of gas-permeable, or breathable, non-woven material.

As used herein, the term "breathable" refers to material which is permeable to water vapor having a minimum water vapor transmission rate (WVTR) of about 300 $g/m^2/24$ hours, calculated in accordance with ASTM Standard E96-80.

In preferred embodiments, a commonly available sterilization indicator can be placed within the sterilization bag for easy determination of the sterilization status of the contents therein.

The present invention provides at least about an 85% bacterial filtration efficiency to the sterilizable object. More preferably, the present invention provides at least about an 90% bacterial filtration efficiency to the sterilizable object, and most preferably at least about an 95% bacterial filtration efficiency to the sterilizable object.

The invention provides that the material of the sterilization bag can be constructed of polyolefin. In preferred embodiments, the material of the outer bag and/or the inner sterilization wrap can be preferably a SMS laminate, that can be electreted as described for example in U.S. Pat. No. 5,401,446. Electreting involves subjecting the material to a pair of electrical fields having opposite polarities. Each electrical field forms a corona discharge which is imparted to the material. Other means of electreting the material are well-known, such as thermal, liquid contact and electron beam methods.

In preferred embodiments, the material of the sterilization bag comprises a meltblown layer between first and second spunbonded layers. Preferably, the material is between about 0.6 and 6 ounces per square yard. The invention provides that the spunbonded layers can be between about 0.25 and 2.0 ounces per square yard and the meltblown layer can be between about 0.1 and 2.0 ounces per square yard. More preferably, the material is about 2.2 ounces per square yard, such that the spunbonded layers are about 0.85 ounces per square yard and the meltblown layer is about 0.5 ounces per square yard.

The sterilization bag can be formed from a sheet of material folded once and side-sealed ultrasonically or by other means, such as heat sealing, stitching, or adhering, to define a pouch with an opening for receiving therein a sterilizable object. Construction and shape of the sterilization bag can vary widely depending upon the intended size of the sterilizable objects which are to be inserted therein. For example, one end of the folded material may be longer in order to provide a foldable flap to selectively cover the opening of the pouch. The sterilization bag is intended to be re-used, therefore, construction must permit the placement and removal of sterilizable objects without destroying the bacterial filtration integrity of the bag.

The invention further provides methods of sterilizing an object, and methods of using an outer sterilization bag, comprising, first placing the object inside an inner sterilization wrap, and then inserting the object within the sterilization wrap into a re-usable outer sterilization bag. The re-usable outer sterilization bag has an outside surface and an inside surface defining a pouch with an opening therein for receiving the inner sterilization wrap and sterilizable object. The re-usable outer sterilization bag is made from a breathable, non-woven material. The outer sterilization bag containing the inner sterilization wrap, containing the object, is then sterilized by available means.

Several patents have been mentioned herein, which are hereby incorporated by reference in their entireties. The present invention is intended to be demonstrated, but not limited, by the following examples.

EXAMPLES

The following test procedure was performed to determine the Bacterial Filtration Efficiency (BFE) of various filtration materials, employing a ratio of the bacterial challenge counts to sample effluent counts, to determine percent bacterial filtration efficiency (% BFE). This procedure provided a more severe challenge to most filtration materials than would be expected in normal use. This test procedure allowed a reproducible bacterial challenge to be delivered to test materials.

The BFE test described below was performed by Nelson Laboratories (Salt Lake City, Utah). The sterilization was carried out in a STERRAD® gas plasma sterilizer unit available from Advanced Sterilization Products, a division of Johnson & Johnson Medical, Inc. (Irvine, Calif.).

Test Procedure

A culture of *Staphylococcus aureus* was diluted in 1.5% peptone water to a precise concentration to yield challenge level counts of 2200±500 colony forming units (CFU) per test sample. The bacterial culture suspension was pumped through a 'Chicago' nebulizer at a controlled flow rate and fixed air pressure. The constant challenge delivery, at a fixed air pressure, formed aerosol droplets with a mean particle size (MPS) of approximately 3.0 um. The aerosol droplets were generated in a glass aerosol chamber and drawn through a six-stage, viable particle, Andersen sampler for collection. The collection flow rate through the test sample and Andersen sampler was maintained at 28.3 LPM (1 CFM). Test controls and test samples were challenged for a two minute interval.

The delivery rate of the challenge also produced a consistent challenge level of 2200±500 CFU on the test control plates. A test control (no filter medium in the airstream) and reference material are included after 7–10 test samples. The Andersen sampler, a sieve sampler, impinged the aerosol droplets onto six agar plates based on the size of each droplet. The agar medium used was soybean casein digest agar (SCDA). The agar plates were incubated at 37° C.±2° C. for 48±3 hours and the colonies formed by each bacteria laden aerosol droplet counted and converted to 'probable hit' values using the hole conversion chart provided by Andersen. These converted counts were used to determine the average challenge level delivered to the test samples. The distribution ratio of colonies for each of the six agar plates were used to calculate the mean particle size (MPS) of the challenge aerosol.

The filtration efficiencies were calculated as a percent difference between test sample runs and the control average using the following equation:

$$BFE\% = \frac{C-T}{C} \times 100$$

Where:
C=Average of control values.
T=Count total for test material.

This test procedure produces a more severe challenge to most filtration materials than would be expected in normal use. The purpose of this procedure is not to optimize the filtration efficiency, but to consistently measure, as accurately as possible, the differences between materials, or differences in the same material over time.

Several Quality Control steps have been taken to consistently perform the Bacterial Filtration Efficiency procedure. First, the test control average, determined from control runs where no filter medium is in the airstream, must be maintained at 2200±500 CFU for the test to be valid. Additionally, at least one reference material is included with every 7–10 samples tested. Statistical evaluation of these reference material data were recorded on control charts. The reference material must be within the upper and lower control limits (±3 standard deviations) established for the test.

The outer sterilization bags used herein were made from a non-woven composite layer material. The material was about 2.2 ounces per square yard (osy) of spunbonded/meltblown/spunbonded (SMS). Both the spunbonded layers had a basis weight of 0.85 osy, and the meltblown layer had a basis weight of 0.50 osy (See Brock et al., U.S. Pat. No. 4,041,203). The invention contemplates that other weights can be used as well as other barrier materials to make the bag. The material was made into a bag by folding the sheet in half and ultrasonically sealing the two opposing sides, thereby leaving a single opening.

The inner sterilization wraps used herein were also made from a non-woven SMS composite layer material. The inner sterilization wrap SMS materials used herein are known commercially as KIMGUARD® sterile wraps, and were tested with (Table I) and without (Table II) ZELEC® antistatic.

The electreting of materials was performed as described in U.S. Pat. No. 5,401,446. Typical conditions were about 68.9° F. and 61% RH. The top electrode was at about 15.0 KV and the bias electrode at about 0.0 KV for the first set of electrodes and about 18.0 KV for the top electrode and about 0.0 KV for the bias electrode for the second set of electrodes. The temperature varied from about 68.8° to 70.2° F., and the % RH from about 40.0 to 63.0%. The top electrodes varied from about 18 to 10 KV and the bias electrodes were approximately constant.

Each bag used was exposed to a full gas plasma sterilization procedure at least six times before being used in the test described herein. There was no apparent damage to the bag as noted by visual inspection and FESEM (Field Emission Scanning Electron Microscope) inspection of the fibers.

TABLE I

SMS material for sterilization wraps and sterilization bags without surface treatment.

| Electreted Bag | Non-Electreted Bag | Electreted Wrap | Non-Electreted Wrap | BFE % | SD |
|---|---|---|---|---|---|
|  | √ |  | √ | 88.14 | ±1.59 |
|  | √ | √ |  | 96.24 | ±1.49 |
| √ |  |  | √ | 88.27 | ±2.33 |
| √ |  | √ |  | 92.91 | ±0.72 |

Each sample provided eleven analyses to give a 98% confidence level for the statistical analysis. The data suggests that electreting the sterilization wrap had a major effect on the BFE. However, electreting the sterilization bag had no effect on the BFE. Therefore, the results demonstrate that when using materials not treated with antistatic, the optimum combination for BFE is a non-electreted sterilization bag with an electreted sterilization wrap.

TABLE II

SMS inner wrap material surface treated with ZELEC ® antistatic

| Electreted Bag | Non-Electreted Bag | Electreted Wrap | Non-Electreted Wrap | BFE % | SD |
|---|---|---|---|---|---|
| | √ | | √ | 92.05 | ±1.08 |
| | √ | | √ | 92.24 | ±1.63 |
| | √ | | √ | 91.71 | ±1.08 |
| | √ | √ | | 96.52 | ±0.56 |
| | √ | √ | | 96.46 | ±0.96 |
| | √ | √ | | 96.33 | ±1.21 |
| √ | | | √ | 90.79 | ±1.10 |
| √ | | | √ | 92.31 | ±0.73 |
| √ | | | √ | 91.03 | ±0.88 |
| √ | | √ | | 97.38 | ±0.89 |
| √ | | √ | | 98.31 | ±0.63 |
| √ | | √ | | 98.31 | ±0.56 |

Again, each sample provided eleven analyses to give a 98% confidence level for the statistical analysis. Therefore, these data suggest that an electreted sterilization wrap had a considerable effect on the BFE. Surprisingly, in this Example using inner wrap materials treated with antistatic, an electreted sterilization bag in combination with an electreted sterilization wrap showed a statistical improvement in filtration efficiency over a non-electreted sterilization bag.

While the invention has been described in detail with respect to the specific embodiments thereof, it will be appreciated that those skilled in the art may readily conceive of alterations and equivalents to these embodiments. Accordingly, the scope of the present invention should be assessed as that of the appended claims and any equivalents thereto.

I claim:

1. A device for sterilization comprising:
   an inner sterilization wrap; and
   a re-usable outer sterilization bag comprising an outside surface and an inside surface, the inside surface defining a pouch with an opening for receiving a sterilizable object wrapped within the inner sterilization wrap, wherein the bag is made from a breathable, non-woven material.

2. The device of claim 1, further comprising a sterilization tray substantially enclosed by the inner wrap.

3. The device of claim 1, further comprising an antistatic treatment on the inner sterilization wrap or the outer sterilization bag.

4. The device of claim 1, wherein the outer bag is electreted.

5. The device of claim 1, wherein the inner wrap is electreted.

6. The device of claim 1, wherein the inner wrap and the outer bag are electreted.

7. The device of claim 1, the inner sterilization wrap having at least about an 85% bacterial filtration efficiency.

8. The device of claim 1, the inner sterilization wrap having at least about an 90% bacterial filtration efficiency.

9. The device of claim 1, the inner sterilization wrap having at least about an 95% bacterial filtration efficiency.

10. The device of claim 1, wherein the material of the bag is a polyolefin.

11. The device of claim 10, wherein the material of the bag comprises a meltblown layer disposed between a first spunbonded layer and a second spunbonded layer.

12. The device of claim 1, wherein the material of the bag has a basis weight of between about 0.6 and 6 ounces per square yard.

13. The device of claim 11, wherein each of the spunbonded layers has a basis weight of between about 0.25 and 2.0 ounces per square yard and the meltblown layer has a basis weight of between about 0.1 and 2.0 ounces per square yard.

14. The device of claim 1, wherein the material of the bag has a basis weight of about 2.2 ounces per square yard.

15. The device of claim 11, wherein the basis weight of each of the spundbonded layers is about 0.85 ounces per square yard and the basis weight of the meltblown layer is about 0.5 ounces per square yard.

16. The device of claim 1, wherein the bag is formed from a sheet of material which is folded and ultrasonically side-sealed.

17. A method of using a sterilization bag comprising the steps of:
   a) placing a sterilizable object inside an inner sterilization wrap;
   b) inserting the object within the sterilization wrap into a re-usable outer sterilization bag, said bag comprising an outside surface and an inside surface defining a pouch with an opening for receiving the inner sterilization wrap and sterilizable object, wherein the bag is made from a breathable nonwoven material; and
   c) subjecting the bag, the inner sterilization wrap and the sterilizable object to a sterilization cycle.

18. The method of claim 17, wherein the inner sterilization wrap and/or the outer sterilization bag is electreted and further comprises an antistatic treatment on the inner sterilization wrap and/or the outer sterilization bag.

19. The method of claim 17, wherein the outer sterilization bag is capable of providing at least about an 85% bacterial filtration efficiency to the sterilizable object.

20. The method of claim 17, wherein the material of the bag comprises a polyolefin meltblown layer between first and second polyolefin spunbonded layers, wherein the basis weight of each of the spunbonded layers is between about 0.25 and 2.0 ounces per square yard and the basis weight of the meltblown layer is between about 0.1 and 2.0 ounces per square yard.

21. The device of claim 11 wherein at least one of the spunbonded layers has been prebonded.

22. A system for sterilization comprising:
   an inner sterilization wrap; and
   a re-usable outer sterilization bag configured to receive a sterilizable object wrapped within the inner sterilization wrap, the re-usable outer sterilization bag being constructed from a breathable, nonwoven material;
   wherein, after sterilization of the re-usable outer sterilization bag, the sterilizable object and the inner sterilization wrap, the outer sterilization bag may be opened in a manner which permits the outer sterilization bag to be re-used.

23. The sterilization system of claim 22, wherein the re-usable outer sterilization bag is comprised of a material having a basis weight of between about 0.6 and 6 ounces per square yard.

24. The sterilization system of claim 22, wherein the re-usable outer sterilization bag is comprised of a material having a basis weight of about 2.2 ounces per square yard.

25. The sterilization system of claim 22, wherein the re-usable outer sterilization bag comprises a meltblown layer disposed between a first spunbonded layer and a second spunbonded layer.

26. The sterilization system of claim 25, wherein each spunbonded layer has a basis weight of between about 0.25 and 2.0 ounces per square yard and the meltblown layer has a basis weight of between about 0.1 and 2.0 ounces per square yard.

27. The sterilization system of claim 25, wherein each spundbonded layer has a basis weight of about 0.85 ounces per square yard and the meltblown layer has a basis weight of about 0.5 ounces per square yard.

28. The sterilization system of claim 22, wherein at least one spunbonded layer has been prebonded.

29. The system of claim 22 wherein the inner sterilization wrap is electret treated.

30. The system of claim 29 wherein the outer re-usable bag has been electret treated.

31. The system of claim 22 wherein the outer re-usable bag has been electret treated.

32. The system of claim 22 wherein an anti-static treatment has been applied to the inner sterilization wrap.

33. The system of claim 32 wherein the inner sterilization wrap has been electret treated.

34. The system of claim 33 wherein the outer re-usable bag has been electret treated.

35. The system of claim 32 wherein the outer re-usable bag has been electret treated.

36. The system of claim 22, the inner sterilization wrap having a bacterial filtration efficiency of at least about 85%.

37. The system of claim 36 the inner sterilization wrap having a bacterial filtration efficiency of at least about 90%.

38. The system of claim 37, the inner sterilization wrap having a bacterial filtration efficiency of at least about 95%.

* * * * *